United States Patent [19]
Yale et al.

[11] Patent Number: 6,159,150
[45] Date of Patent: Dec. 12, 2000

[54] MEDICAL DIAGNOSTIC ULTRASONIC IMAGING SYSTEM WITH AUXILIARY PROCESSOR

[75] Inventors: Kenneth R. Yale, Saratoga; Douglas J. Gallinat, San Jose; Stefan J. A. Schmitz, Milpitas, all of Calif.

[73] Assignee: Acuson Corporation, Mountain View, Calif.

[21] Appl. No.: 09/196,207

[22] Filed: Nov. 20, 1998

[51] Int. Cl.$^7$ ........................................................ A61B 8/00
[52] U.S. Cl. ............................................................ 600/437
[58] Field of Search .................................. 600/437, 438, 600/443, 449, 448, 472; 128/916

[56] References Cited

U.S. PATENT DOCUMENTS

| | | | |
|---|---|---|---|
| 5,256,908 | 10/1993 | Averbuch et al. | 367/99 |
| 5,331,580 | 7/1994 | Miller et al. | 364/708.1 |
| 5,715,823 | 2/1998 | Wood et al. | |

OTHER PUBLICATIONS

QV100 Quickview Module, Acuson Corporation, 1994.
AEGIS Digital Image and Data Management System—QV150 Module, Acuson Corporation, 1997.

Primary Examiner—William E. Kamm
Assistant Examiner—Maulin Patel
Attorney, Agent, or Firm—Brink Hofer Gilson & Lione

[57] ABSTRACT

An ultrasonic imaging system includes an auxiliary processor that is connected to the imaging system by an open-standard, high-speed digital data channel. The system processor of the imaging system directs some processing tasks to the imaging system for execution in the conventional manner. Other processing tasks (often associated with computationally intensive applications) are automatically routed to the auxiliary processor for execution. The data channels between the system processor and the auxiliary processor allow high-speed exchange of live video information such that the identity of the processor performing a particular application is transparent to the user.

16 Claims, 3 Drawing Sheets

Microfiche Appendix Included
(1 Microfiche, 38 Pages)

MEDICAL DIAGNOSTIC ULTRASONIC IMAGING SYSTEM WITH AUXILIARY PROCESSOR

IDENTIFICATION OF MICROFICHE APPENDIX

This specification includes a microfiche appendix including 38 frames on 1 fiche.

BACKGROUND

The present invention relates to medical diagnostic ultrasonic imaging systems, and in particular to auxiliary processors for such systems that can be used to expand system resources efficiently.

Modern medical diagnostic ultrasound imaging systems are tightly integrated and highly engineered products. During the life of these products digital processing technology often improves in unforeseen ways. Such technological improvement can obsolete the basic internal resources of the imaging system. For example, modern ultrasound imaging systems include central processing units (CPU's), memory, input/output channels, and operating systems, all of which can quickly become limiting factors. For example, existing CPU's in 1998 are at least 20 times faster than those available in 1993. Memory grows ever less expensive, and the ability of a relatively slow CPU to use large memory effectively is less than that of a newer, faster CPU. State-of-the-art disk interfaces of 1998 provide more than ten times the performance of disk interfaces of 1993. Newer types of disk interfaces may make older ones completely obsolete.

Furthermore, the conventional resources of an ultrasound imaging system provide limited input/output flexibility. Circuit board space and design flexibility are expensive, and it is difficult to justify a spare slot on a proprietary bus for undefined future expansion. Furthermore, it is often not even possible to predict which type of a bus slot should be provided. For example, it was not possible in 1993 to predict that USB or IEEE 1394 Firewire slots would be desirable in 1998.

Furthermore, a conventional, tightly integrated ultrasonic imaging system, including its underlying operating system support, often limit the flexibility to innovate and explore alternatives. Generally speaking, third-party software operating systems and applications are difficult or almost impossible to use with a conventional tightly integrated ultrasound imaging system.

The traditional approach to these problems is to increase the engineering effort to redesign imaging system hardware to improve the CPU memory and I/O performance. This effort can be effective, but it often provides only a partial or temporary solution. Additional engineering effort required for software and operating system enhancement can extend product development cycles to the point where the cost of the engineering effort exceeds the anticipated return on the investment.

One prior-art approach to this problem is the Acuson QV100 system. The QV100 system provides a proprietary serial and two-way video connection between an ultrasound imaging system and a Macintosh computer. The Macintosh computer is programmed to perform image captures and to save the images to an image server. Image transfers are performed via a two-way analog channel from the ultrasound system to additional video frame grabbing hardware on the Macintosh computer. This device is limited to performing only image capture, display, and server functions. Alternate ultrasound applications are not part of this device. The QV100 system simply acts as a frame grabbing and storage system that is added to the conventional ultrasound imaging system capabilities.

SUMMARY

The present invention is directed to an improved ultrasound imaging system that includes an auxiliary processor as described below to dramatically increase the efficiency and ease of enhancing ultrasound system performance. The following paragraph is intended only by way of general introduction, and is not intended to limit the scope of the following claims.

The preferred embodiment described below includes a conventional medical diagnostic ultrasound imaging system that is connected by a high-speed data channel to an auxiliary processor, which is preferably a conventional personal computer or work station. The auxiliary processor can readily be expanded, modified, updated and programmed to provide the desired processing capabilities to the ultrasound imaging system. The high-speed data channel allows ultrasound exam information, including ultrasound image information, to be transferred between the imaging system and the auxiliary processor such that the identity of the processor performing any particular task is transparent to the user.

DETAILED DESCRIPTION OF THE PRESENTLY PREFERRED EMBODIMENTS

Figure 1:
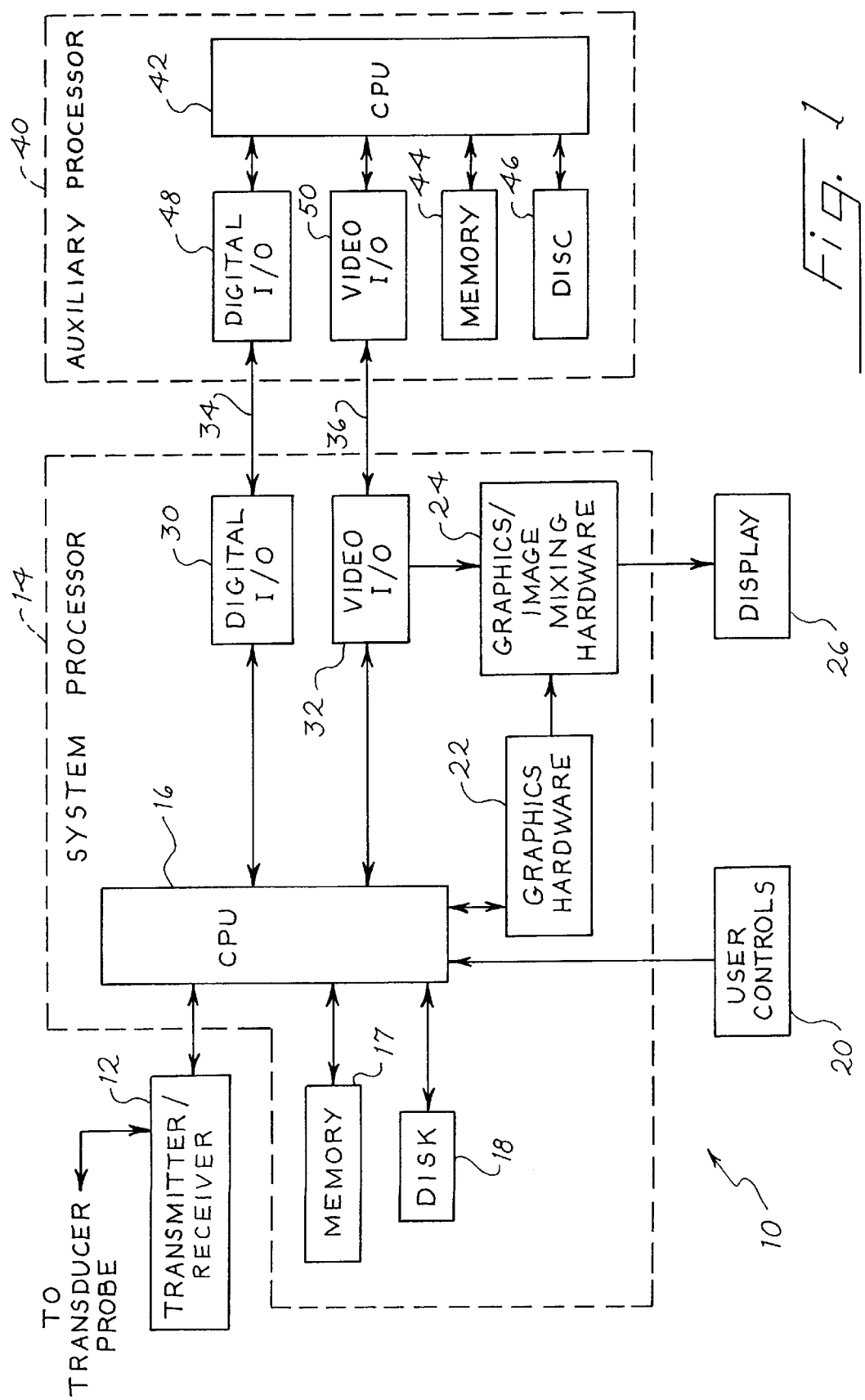
FIG. 1 is a block diagram of a medical diagnostic ultrasound imaging system that incorporates a preferred embodiment of this invention.

The preferred embodiment shown in FIG. 1 provides an integrated system including a generally conventional ultrasound imaging system coupled to an auxiliary processor via a high-speed data channel. This system allows the live video output of the auxiliary processor (which may often be newer and more technologically advanced than the system processor of the imaging system) to be displayed to a sonographer operating the ultrasound system. The sonographer's computer interactions (typically, but not limited to keyboard, trackball, mouse, buttons, slider controls, knobs, ultrasound-specific transducers, foot switch, and voice input) are received by the existing ultrasound system, but may, under software control described below, be directed to the auxiliary processor for execution. In addition, the system processor 14 may offload a processing task to the auxiliary processor 40. The perception of the sonographer is that he is dealing with an ultrasound system in the conventional manner, when in fact the sonographer is controlling the ultrasound system as well as the auxiliary processor, or both, as needed by the particular application.

Turning now to FIG. 1, the preferred embodiment of this invention includes an ultrasound imaging system 10 and an auxiliary processor 40. The imaging system 10 includes a transmitter/receiver 12 that includes an output port that is connected in the conventional manner to any suitable ultrasound transducer probe. The transmitter/receiver is in turn connected to a system processor 14. The system processor includes a central processing unit (CPU) 16 which is coupled in the conventional manner with a memory 17 and a disk storage system 18. The system processor 14 is responsive to user controls 20 which can include any suitable device for allowing a user to provide information including commands to the system processor. The CPU 16 is coupled by conventional graphics hardware 22 and graphics/image mixing hardware 24 to a display 26 such as a video monitor.

The elements 12 to 26 described above can be conventional, and can be embodied as any of a wide variety of ultrasound imaging systems. Presently, the Sequoia ultrasound imaging system of Acuson Corporation is preferred. Since many variations of elements 12 to 26 are well known to those skilled in the art, they will not be described in greater detail here.

In this embodiment the CPU 16 additionally is coupled to digital I/O hardware 30 and video I/O hardware 32. The digital I/O hardware 30 is connected via a high-speed digital data channel 34 with the auxiliary processor 40, and the video I/O hardware 32 is connected via a video data channel 36 with the auxiliary processor 40.

The auxiliary processor 40 includes a CPU 42 connected a conventional memory 44 and disk storage system 46. The auxiliary processor 40 also includes digital I/O hardware 48 coupled to the high-speed digital data channel 34, and video I/O hardware 50 coupled to the video data channel 36.

The auxiliary processor 40 is preferably an industry standard personal computer or work station running a modern, well supported operating system. Many alternatives are possible, including a Pentium II personal computer or an Alpha personal computer running Windows NT or Linux.

The high-speed digital data channel 34 is used in this embodiment for both image data and control data. This data channel may be implemented in any of the current or planned data bus technologies, including any of the varieties of Ethernet, the universal serial bus (USB), Firewire (IEEE-1394), fiber optics (FDDI), ATM, Frame Relay, and the like. If the high-speed digital data channel 34 is sufficiently fast, video images can be exchanged between the system processor 14 and the auxiliary processor 40 via the digital data channel 34. High quality ultrasound images can be digitally transferred between the system processor 14 and the auxiliary processor 40 as data files over the high-speed digital data channel 34.

The video data channel 36 allows the auxiliary processor 40 to drive the display 26 of the ultrasound system. The video data channel may be any of a number of standard video technologies, such as, RGB-NTSC, RGB-PAL, SVHS-NTSC, SVHS-PAL, and the like. A digital video interface, optionally using digital video compression techniques such as JPEG or RLE, can be used instead of a separate analog channel.

The ACR/NEMA protocol for medical image description has a generally used subset and pattern of use known as DICOM. Some third-party image vendors use DICOM to describe the contents of the files transferred. The system processor 14 can provide a DICOM portal for third-party software to retrieve, send and update ultrasound images and data, if this protocol is used. Alternately, other protocols and associated transfer agents can be used.

In this embodiment, the data channels 34, 36 are dedicated such that they are only used by the system processor 14 and the auxiliary processor 40. In this embodiment the range of each of the data channels 34, 36 is less than 15 feet such that the auxiliary processor 40 remains physically associated with the system processor 14. Of course, it is possible to use data channels that are not dedicated or that are longer than this range.

Figure 2:
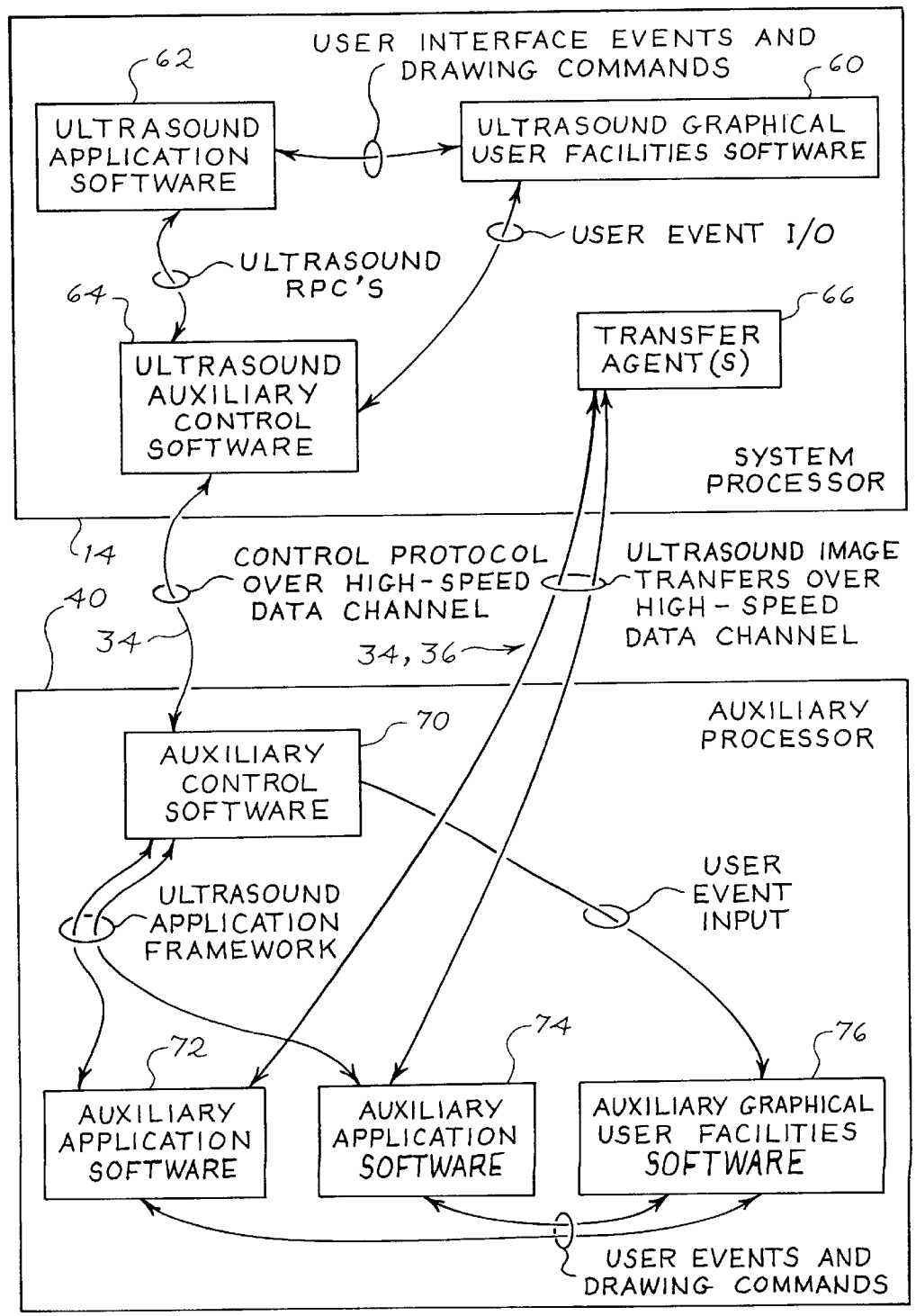
FIG. 2 is a block diagram showing the interaction of major software components of the embodiment of FIG. 1.

One preferred embodiment of the software used on the system processor 14 and the auxiliary processor 40 is shown in FIG. 2. As shown in FIG. 2, the system processor 14 includes ultrasound graphical user facility software 60 and ultrasound application software 62. User interface events and drawing commands as processed by the ultrasound graphical user facility software 60 are applied to the ultrasound application software 62 to cause the ultrasound application software 62 to perform desired imaging tasks. For example, the ultrasound application software 62 can control the transmitter/receiver to acquire one or more two-dimensional frames of ultrasound image information in a user-designated imaging mode using user-designated imaging parameters, without assistance from the auxiliary processor 40.

The system processor 14 also includes ultrasound auxiliary control software 64. The ultrasound auxiliary control software 64 is under control of the ultrasound application software 62. When desired by the ultrasound application software 62, the ultrasound auxiliary control software 64 converts user I/O events into a data format understood by the auxiliary processor 40. The ultrasound auxiliary control software 64 then sends the converted events via the high-speed digital data channel 34. In addition, the ultrasound application software 62 can synthesize user I/O event messages and forward these events to the ultrasound auxiliary control software 64 for conversion and forwarding to the auxiliary processor 40 as described above. Furthermore, the ultrasound application software 62 can direct the ultrasound auxiliary control software 64 to synthesize a user I/O event message itself, after which conversion and forwarding to the auxiliary processor 40 occurs as described above. The ultrasound auxiliary control software 64 also acts as a focal point for ancillary protocol and application communication tasks, including the following:

Establishing and maintaining the data channel connection with the auxiliary processor 40;

Matching the protocol versions used by the processors 14, 40;

Shutting down the auxiliary computer by synchronizing the ultrasound power off cycle to prevent damage to the file system of the auxiliary computer;

Message logging;

Controlling video and user interaction switching between the processors 14, 40;

Acting as a conduit and providing synchronization for application-specific messages.

By way of example but not limitation, such messages can include ultrasound image positioning information, ultrasound image names, ultrasound study names, results of voice control from the auxiliary processor to drive the system processor, selection of specific auxiliary applications to be executed by the auxiliary processor, parameters for the auxiliary applications executed by the auxiliary processor, control over sensor positioning devices, and retrieval of sensor position data.

The system processor 14 also includes one or more transfer agents 66 for image transfer. As explained above, a DICOM server, an NFS server, an FTP server, or an SMB server can be used for digital image transfer.

As shown in FIG. 2, the auxiliary processor includes auxiliary control software 70, one or more auxiliary applications 72, 74, and auxiliary graphical user facility software 76.

The auxiliary control software 70 accepts converted user interactions from the ultrasound auxiliary control software 64 received via the high-speed digital data channel 34, converts them again if necessary to a form understandable by the local operating system and/or the auxiliary graphical user facilities software 76, and forwards them to the local operating system and/or the auxiliary graphical user facilities software 76. In this manner, the converted user interactions can be used to control the auxiliary processor 40 in any manner supported by the local operating system and/or the auxiliary graphical user facilities software 76. The auxiliary control software 70 can also initiate tasks not apparent to the sonographer, such as the background transfer and processing of ultrasound data in anticipation of future need of this processing.

The auxiliary control software 70 also acts as a focal point for ancillary protocol and application communication tasks, including the following:

- establishing and maintaining the data channel connection with the system processor 14;
- providing the protocol versions used by the auxiliary processor 40 to the system processor 14;
- initiating and coordinating the shutdown of the auxiliary processor 40, especially when the auxiliary processor 40 uses switched power from the ultrasound imaging system 10;
- starting, controlling, and stopping various programs that run on the auxiliary processor 40, such as the auxiliary applications 72, 74;
- acting as a conduit and providing synchronization for application-specific messages.

The auxiliary control software 70 not only receives and responds to user interactions and messages initiated by the ultrasound application software 62, but it can also be the initiator of messages. For instance, when a processing task is completed, an error is detected, or some other condition or event has happened on the auxiliary processor 40, the auxiliary control software 70 can initiate and send messages to the ultrasound auxiliary control software 64 via the high-speed digital data channel 34. The ultrasound auxiliary control software 64 will then take appropriate action, which may for example include the step of forwarding the message to the ultrasound application software 62.

These interactions are collectively known as the ultrasound application framework. This framework allows generic control over arbitrary third-party software packages that run on the auxiliary processor 40.

The auxiliary applications 72, 74 use the capabilities of the auxiliary processor 40 to perform ultrasound image operations or other tasks. User-visible output is directed to the video card of the auxiliary processor 40 and sent to the ultrasound system processor 14 for display.

Generally speaking, at least one of the auxiliary applications will perform complex image processing on image information supplied by the imaging system, and will then automatically return a result of the complex processing to the imaging system for inclusion in the exam record generated by the imaging system. As used herein, "complex image processing" refers to manipulation of image information, and is distinguished from simple image processing such as image storing, retrieving and archiving. Examples of complex image processing include generating 3-D renderings from 2-D images, generating extended fields of view, generating positional information for 2-D images, generating parameters from ultrasonic images (such as the volume of blood pumped by the heart per stroke or the length of a body structure), and so forth. Examples of results of such processing may include images, numerical results, or other results. Examples include 3-D renderings, extended field of view images, and calculated parameters.

The ultrasound application software 62 of the system processor 14 decides when to switch user interactions from the system processor 14 to the auxiliary processor 40. The ultrasound application software 62 decides what images are to be dealt with, and what software is to be run on the auxiliary processor 40. The ultrasound application software 62 decides when to terminate user interactions with the auxiliary processor 40, and it programs the system processor 14 to accept video input from the auxiliary processor 40 and to place this video input on the display 26 of FIG. 1.

The system processor 14 uses the graphic/image mixing hardware 24 (FIG. 1) to overlay the alternative video input from the auxiliary processor 40 with text or graphics from the system processor 14. In this way a consistent visual experience is presented to and preserved for the sonographer. Thus, the graphic/image mixing hardware 24 operates as a means for blending exam information from the auxiliary processor 40 with additional exam information from the system processor 14. This blending can be performed using any suitable hardware and software, as long as the desired blended result is obtained. Often, the additional exam information from the system processor 14 is limited to non-image graphical information such as user interface elements, legends, notations, soft key labels, and other graphics.

The digital data channel 34 forms a first means for supplying first digital ultrasound exam information to the auxiliary processor 40. As mentioned above, this digital ultrasound exam information may include digital ultrasound image information, though this is not required. The data channels 34, 36 both function as a means for supplying ultrasound exam information from the auxiliary processor 40 to the system processor 14, including ultrasound image information. As mentioned above, the video data channel 36 may be integrated into the digital data channel 34, in the event the digital data channel 34 has adequate capacity.

Preferably, the data channels 34, 36, are both open standard data channels. That is, the electrical, physical, and transport format protocol standards for the data channels are publicly available. Thus, open standard data channels are distinguished from proprietary data channels of the type conventionally used in tightly integrated ultrasound imaging systems of the prior art.

Thus, the ultrasound application software 62 and the ultrasound auxiliary control software 64 cooperate to form a means for automatically sending commands associated with first user controls to the system processor 14 and commands associated with second user controls to the auxiliary processor 40. For example, one of the first user controls can result in commands associated with the acquisition of a conventional two-dimensional ultrasound image, and such commands can be executed by the ultrasound application software 62 in the system processor 14. Similarly, one of the second user controls can result in commands associated with more computationally intensive tasks such as three-dimensional rendering or extended field of view processing, and these commands can be transferred automatically by the software 62, 64 to the auxiliary processor 40. The software 62, 64 can be considered an example of means for automatically directing separate processing tasks to respective ones of the processors 14, 40. Because of the high speed data channel 34 and the high speed video channel 36, this is done in a manner such that the identity of the processor 14, 40 that is performing any specific processing task is transparent to the user. As used herein, the term "transparent" is intended to convey that user interaction with the auxiliary processor 40 is comparable to user interaction with the system processor 14 and is not substantially slower or less convenient. In some cases the identity of the specific processor performing a task may be made known to the user while retaining the transparent nature of the processing. Alternately, the user may be unaware that the imaging system even includes an auxiliary processor.

Figure 3:
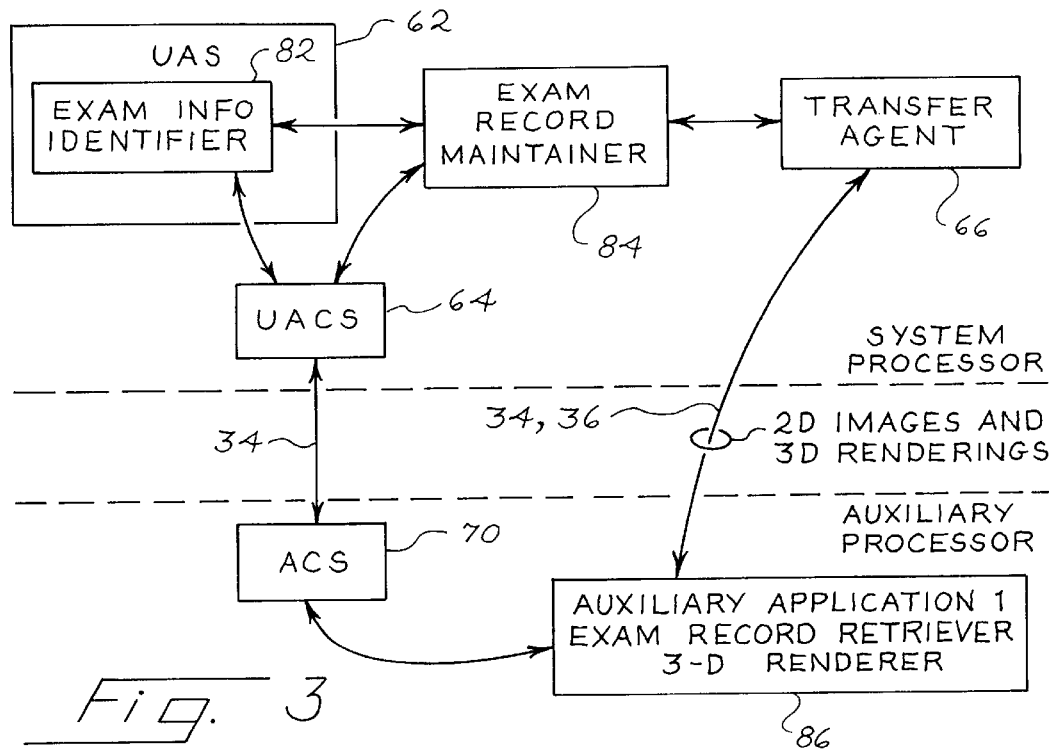
FIGS. 3 and 4 are block diagrams of two additional embodiments of some of the software components of FIG. 2.
Figure 4:
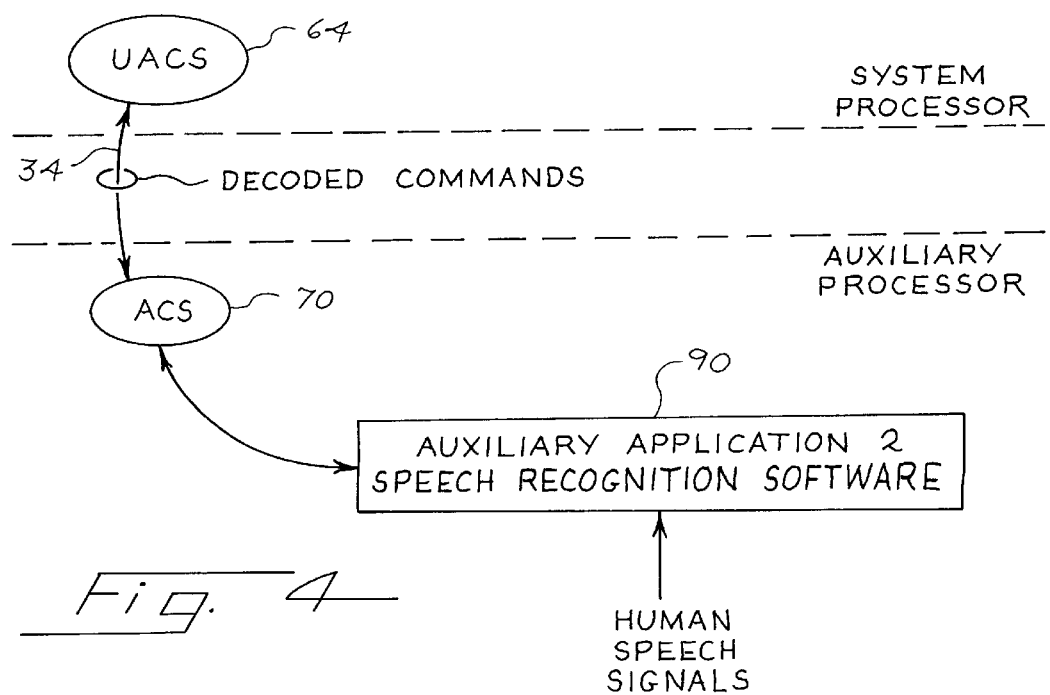

FIGS. 3 and 4 relate to two specific examples of auxiliary applications that can be used with this invention, together with related components of the system processor. FIG. 3 relates to an auxiliary application 86 that includes a system for rendering 3-D views of an array from two-dimensional images. In this embodiment, the ultrasound application software 62 includes an exam information identifier 82, and the system processor further includes an exam record maintainer 84. The exam information identifier 82 can for example identify the specific two-dimensional images that are to be used for a three-dimensional rendering. The exam information identifier 82 is responsive to the user controls. For example, the user may enter a command requesting a three-dimensional rendering of a specific imaged region. These two-dimensional images may be acquired in any suitable manner, stored in the system processor, and then identified by the identifier 82. This identifier information is applied via the high speed digital data channel 34 to the auxiliary control software (ACS) 70. The auxiliary control software 70 supplies the identifiers to the auxiliary application 86. The auxiliary application 86 includes an exam record retriever and a 3-D renderer. The exam record retriever uses the identifiers provided via the data channel 34 to retrieve the identified two-dimensional images from the system processor via the transfer agent 66. The retrieved two-dimensional images are then used by the 3-D renderer to generate a result, in this case a three-dimensional rendering. The three-dimensional rendering is then automatically returned to the exam record maintainer 84 via the transfer agent 66. The exam record maintainer then adds this three-dimensional rendering to the exam record for the appropriate exam. Additionally, the three-dimensional rendering is displayed on the display of the ultrasound imaging system. The three-dimensional rendering may also be transferred back to the system processor as an analog signal.

FIG. 4 relates to another auxiliary application 90 that includes speech recognition software. The speech recognition software 90 responds to human speech signals generated with the use of a microphone (not shown) to recognize machine commands given orally by the user of the ultrasonic imaging system. These machine commands are then transmitted via the auxiliary control software 70 and the data channel 34 to the ultrasound auxiliary control software 64. The software 64 then applies the decoded commands to the appropriate subsystem of the system processor to ensure that the decoded commands are executed by the imaging system.

The embodiments described above provide the capability for many alternative ultrasound resources. These alternative ultrasound resources can be used to expand the capabilities of a system processor 14, and therefore the imaging system of which system processor 14 is a part, in an economical, efficient and easy to implement way. Some of the many alternate ultrasound resources and advantages that can be provided with the auxiliary processor 40 are as follows:

Growth—Off the shelf computing power can be added without redesigning the system processor 14.

Flexibility—A broad spectrum of products that vary greatly in cost and performance can be constructed by properly selecting the capabilities (hardware, I/O capabilities, and software) of the auxiliary processor 40. As technology advances, the auxiliary processor 40 can easily be enhanced for increased performance.

Cost Reduction—In the embodiment described above, the resources of the system processor 14 can be limited to the bare minimum needed to meet live ultrasound interaction performance requirements. This feature can substantially reduce cost of the system processor 14, since functions that are not critical to selected modes of operation of the ultrasound imaging system can be performed by the auxiliary processor 40.

Stability—The auxiliary processor 40 is an easily separated module that can be upgraded by commercially available vendors, freeing the designers of the ultrasound imaging system to focus time and energy on ultrasound-specific hardware.

Three-Dimensional Rendering—Three-dimensional rendering of ultrasound images is a computationally intensive process that is well suited for execution by the auxiliary processor 40, using DICOM ultrasound images that are digitally acquired and transferred.

Positioning Information—The auxiliary processor 40 is well suited to acquire transducer position information. For example, an absolute position measuring system for locating an ultrasound probe in space and time can be installed on the auxiliary processor to store time-stamped position data for the probe. The time-stamped position data may be associated with time-stamped ultrasonic images, either by the system processor 14, by the auxiliary processor 40, or by another processor.

Extended Field of View Processing—With extended field of view processing, ultrasound data for multiple images are combined by longitudinally splicing one image onto another to increase the field of view. The auxiliary processor 40 makes live presentation of extended field of view images feasible with a short development schedule and a low risk to the existing ultrasound system.

Alternate User Interfaces—The auxiliary processor 40 can be used to implement user interactions from alternative resources that would be cumbersome to develop on the system processor 14. Graphical drawing performance and development environments make the auxiliary processor 40 attractive for implementing user interactions such as ultrasound calculation packages, configuration packages and the like.

Voice Input—The auxiliary processor 40 can be used to execute third party voice recognition software, with the output of the voice recognition software sent to the ultrasound imaging machine to drive its user interactions. In this mode of operation, no image signal from the auxiliary processor 40 is used by the system processor 14.

Software Standards—The auxiliary control software 70 controls which programs are run on the auxiliary processor in response to commands from the imaging system as described above. The communication between the auxiliary control software and the auxiliary applications it controls can be made using an open communication standard to allow third-party vendors to provide additional, possibly experimental capabilities to the imaging system, potentially independently of involvement of the manufacturer of the ultrasound imaging system.

The auxiliary processor 40 can also include maintenance software that allows installation, upgrading, and maintenance of the software of the auxiliary processor through direct manipulation of its underlying operating system. The system processor 14 sends keystrokes and other user interaction events to the auxiliary processor 40 and displays the video output of the auxiliary processor 40 on the display of the ultrasound system.

Simply by way of example, the following further details of construction are provided to clarify the best mode of this invention. By way of example, the auxiliary processor 40 can use a 200 MHZ Pentium II CPU, disk memory, and SVGA video I/O hardware. This processor can be used to run auxiliary applications such an application to reconstruct 3D volumes from digital ultrasound images and an application to reconstruct extended width ultrasound images from smaller ultrasound images. Microfiche Appendix A provides further details of implementation for the presently preferred embodiment. Microfiche Appendix B provides pseudo-code describing preferred internal operations that implement several of the functions described above, including the automatic routing of selected user commands to the auxiliary processor for execution of complex image processing tasks, the automatic return of the results of complex image processing tasks from the auxiliary processor to the system processor, and the collecting and processing of voice commands.

As used herein the term "image information" is intended broadly to encompass ultrasound image information in any form, including video information, digital information (either pre- or post-scan conversion) and analog information.

As used herein, the term "ultrasound exam information" is intended broadly to encompass information included in ultrasound exam files such as patient information, exam information, ultrasound image information, 3D renderings, calculations (e.g. heart expulsion volume), image position information, and image annotation information. In many cases ultrasound exam information will include ultrasound image information, though this is not required in all cases.

Of course, it should be understood that many changes and modifications can be made to the preferred embodiment described above. Any suitable programming languages, programming techniques and hardware can be used to implement the functions discussed above, and it is not intended to limit this invention to any particular implementation. The system processor may include multiple CPU's operating in parallel, and similarly the auxiliary processor 40 may include multiple CPUs operating in parallel. If desired, the processors 14, 40 may be physically separated and interconnected by a network, and one or both of the processors 14, 40 may be networked to other systems, such as image archiving systems for example. The auxiliary processor 40 may share components with the system processor 14 such as an A/C power source, a DC power supply, and/or selected peripherals. In these embodiments, the auxiliary processor is mounted to be portable with the imaging system. Also, two or more auxiliary processors 40 can be connected to a single system processor. It is therefore intended that the foregoing detailed description be regarded as illustrative and not as limiting. It is only the following claims, including all equivalents, that are intended to define the scope of this invention.

We claim:

1. In a diagnostic ultrasound imaging system comprising a plurality of user controls, an ultrasonic transmitter/receiver, a display, and a system processor coupled with the user controls, the transmitter/receiver, and the display, the improvement comprising:

an auxiliary processor;

at least one open standard data channel interconnecting the auxiliary processor and the imaging system;

first means for supplying first digital ultrasound exam information from the imaging system to the auxiliary processor via the at least one data channel;

second means for supplying second ultrasound exam information from the auxiliary processor to the system processor via the at least one data channel; and means for blending the second ultrasound exam information supplied to the system processor by the second means with additional exam information supplied by the system processor for display.

2. In a diagnostic ultrasound imaging system comprising a plurality of user controls, an ultrasonic transmitter/receiver, a display, and a system processor coupled with the user controls, the transmitter/receiver, and the display, the improvement comprising:

an auxiliary processor;

at least one open standard data channel interconnecting the auxiliary processor and the imaging system;

first means for supplying first digital ultrasound exam information from the imaging system to the auxiliary processor via the at least one data channel;

second means for supplying second ultrasound image information from the auxiliary processor to the system processor via the at least one data channel; and means, coupled with the system processor and the auxiliary processor, for automatically sending commands associated with first ones of the user controls to the system processor and commands associated with second ones of the user controls to the auxiliary processor via the at least one data channel.

3. In a diagnostic ultrasound imaging system comprising a plurality of user controls, an ultrasonic transmitter/receiver, a display, and a system processor coupled with the user controls, the transmitter/receiver, and the display, the improvement comprising:

an auxiliary processor;

at least one open standard data channel interconnecting the auxiliary processor and the imaging system;

first means for supplying first ultrasound exam information from the imaging system to the auxiliary processor via the at least one data channel;

second means for supplying second ultrasound exam information from the auxiliary processor to the system processor via the at least one data channel;

means, included in the system processor, for automatically directing separate processing tasks to respective ones of the processors for execution such that identity of the processor executing a particular one of the processing tasks is transparent to a user of the imaging system.

4. In a diagnostic ultrasound imaging system comprising a plurality of user controls, an ultrasonic transmitter/receiver, a display, and a system processor coupled with the user controls, the transmitter/receiver, and the display, the improvement comprising:

an auxiliary processor;

at least one open standard data channel interconnecting the auxiliary processor and the imaging system;

first means for supplying first digital ultrasound exam information from the imaging system to the auxiliary processor via the at least one data channel;

second means for supplying second ultrasound exam information from the auxiliary processor to the system processor via the at least one data channel;

third means, responsive to at least some of the user controls, for identifying ultrasound exam information;

fourth means, included in the auxiliary processor and responsive to the third means, for retrieving ultrasound exam information identified by the third means from the system processor via the at least one data channel.

5. In a diagnostic ultrasound imaging system comprising a plurality of user controls, an ultrasonic transmitter/receiver, a display, and a system processor coupled with the user controls, the transmitter/receiver, and the display, the improvement comprising:

an auxiliary processor;

at least one open standard data channel interconnecting the auxiliary processor and the imaging system;

first means for supplying first digital ultrasound exam information from the imaging system to the auxiliary processor via the at least one data channel;

second means for supplying second ultrasound exam information from the auxiliary processor to the system processor via the at least one data channel; and auxiliary application software executed by the auxiliary processor to perform complex image processing on ultrasound images supplied by the imaging system to the auxiliary processor via the first means, and to supply a result of the complex image processing to the imaging system via the second means.

6. In a diagnostic ultrasound imaging system comprising a plurality of user controls, an ultrasonic transmitter/receiver, a display, and a system processor coupled with the user controls, the transmitter/receiver, and the display, the improvement comprising:

an auxiliary processor;

at least one open standard data channel interconnecting the auxiliary processor and the imaging system;

first supplying means for supplying first digital ultrasound exam information from the imaging system to the auxiliary processor via the at least one data channel;

means, included in the auxiliary processor and responsive to the exam information supplied by the first supplying means, for processing the exam information to generate a result; and second supplying means for supplying the result from the auxiliary processor to the imaging system for inclusion in an exam record.

7. In a diagnostic ultrasound imaging system comprising a plurality of user controls, an ultrasonic transmitter/receiver, a display, and a system processor coupled with the user controls, the transmitter/receiver, and the display, the improvement comprising:

an auxiliary processor;

at least one open standard data channel interconnecting the auxiliary processor and the imaging system;

means in the auxiliary processor for converting human speech into commands; and means for supplying the commands to the system processor via the data channel, said system processor operative to control the imaging system in response to the commands.

8. The invention of claim 1, 2, 3, 4, 5, 6 or 7 wherein the at least one data channel comprises a data channel dedicated to the imaging system.

9. The invention of claim 8 wherein the dedicated data channel is characterized by a range that is less than about 15 feet in length such that the auxiliary processor is physically associated with the imaging system.

10. The invention of claim 1, 2, 3, 4, 5, 6 or 7 wherein the auxiliary processor is mounted to be portable with the imaging system.

11. The invention of claim 1, 2, 3, 4, 5, 6 or 7 wherein the auxiliary processor derives at least one of AC power and DC power from the imaging system.

12. The invention of claim 1, 2, 3, 4, 5 or 6 wherein the first digital ultrasound exam information comprises digital ultrasonic image information.

13. The invention of claim 1, 2, 3, 4 or 5 wherein the second ultrasound exam information comprises ultrasonic image information.

14. The invention of claim 1, 2, 3, 4, 5, 6 or 7 wherein the user controls, the ultrasonic transmitter/receiver, the display and system processor are operative to acquire ultrasonic images independently of the auxiliary processor.

15. The invention of claim 1 wherein the additional exam information comprises non-image graphical information.

16. The invention of claim 1 wherein the additional exam information is restricted to non-image graphical information.

* * * * *